United States Patent [19]

De Briere et al.

[11] 4,394,345
[45] Jul. 19, 1983

[54] ULTRASONIC METHOD AND APPARATUS

[75] Inventors: John G. De Briere; Mary M. Lemanowicz; David L. Richardson; Willem Vanderputten, all of San Jose, Calif.

[73] Assignee: General Electric Company, San Jose, Calif.

[21] Appl. No.: 220,431

[22] Filed: Dec. 29, 1980

[51] Int. Cl.³ .................................................. G21C 17/00
[52] U.S. Cl. ....................................... 376/245; 376/249
[58] Field of Search ............... 376/245, 249, 252, 407; 73/622, 624, 625, 627, 628; 417/63

[56] References Cited

U.S. PATENT DOCUMENTS

| | | | |
|---|---|---|---|
| 3,378,456 | 4/1968 | Roberts | 376/407 |
| 3,389,055 | 6/1968 | Hughes | 376/407 |
| 3,780,571 | 12/1973 | Wiesener | 376/249 |
| 3,934,457 | 1/1976 | Clark | 376/249 |
| 3,982,425 | 9/1976 | McLain | 376/249 |
| 3,988,922 | 11/1976 | Clark et al. | 376/249 |
| 4,117,733 | 10/1978 | Gugel | 376/249 |
| 4,131,018 | 12/1978 | Muller et al. | 376/249 |
| 4,149,934 | 4/1979 | Jacobs et al. | 376/249 |

Primary Examiner—Sal Cangialosi
Attorney, Agent, or Firm—Ivor J. James, Jr.; Samuel E. Turner; Raymond G. Simkins

[57] ABSTRACT

An ultrasonic transducer apparatus and method for examining nuclear reactor jet pump beams for cracking. Examination is conducted in situ. An operator lowers a carriage portion of the apparatus into the reactor vessel with a pole. Ultrasonic signals are transmitted through suitable wiring from an external source to the transducer apparatus, which may employ a pitch-catch or pulse-echo mode of ultrasonic examination to test the beams. The carriage holds oppositely disposed pairs of ultrasonic transducers and positions them suitably near the beam to be examined in a proper orientation thereto. The mode of examination is selected by a switching mechanism. The apparatus includes a signal generator, receiver, and visual display.

26 Claims, 9 Drawing Figures

ULTRASONIC METHOD AND APPARATUS

BACKGROUND OF THE INVENTION

This invention relates to the ultrasonic examination of jet pump beams in nuclear reactors by an ultrasonic test apparatus including a carriage holding ultrasonic transducers, which is lowered into the "reactor" as will be discussed herein.

Certain types of nuclear reactors employ as many as twenty downwardly directed jet pumps to circulate reactor water through the core of the reactor vessel during operation. Jet pumps receive driving water from an inlet riser and through a pipe elbow connecting the inlet riser to the jet pump nozzle, as is shown for example in U.S. Pat. Nos. 3,378,456 and 3,389,055, both assigned to General Electric Company. Each pipe elbow is held in position by a jet pump beam, which will be described in substantial detail hereinafter.

The static and dynamic load on jet pump beams including vibrations imposed during reactor operation has been found to cause, in some instances, beam cracking that begins in the upper central portion of the beams. Each jet pump beam holds in place a pipe elbow, which leads reactor water from an inlet riser pipe toward a jet pump nozzle.

Cracking in a jet pump beam threatens the release of a pipe elbow from its normal position, which would impair proper jet pump operation. Accordingly, it is desirable to determine the physical integrity of jet pump beams on a regular basis, as for example by ultrasonic examination. This could be done by dismantling the jet pump beams from the reactor and transporting them to a laboratory for testing. On the other hand, the ultrasonic method and apparatus disclosed herein may instead conveniently be employed for on-site inspection of the jet pump beams within the reactor vessel.

Accordingly, it is an object of this invention to provide test apparatus for ultrasonically examining jet pump beams without requiring their removal from the reactor vessel.

Another object of this invention is to provide an ultrasonic test apparatus that eliminates the need to physically handle and transport jet pump beams for ultrasonic testing and thereby reduces radiation exposure to the personnel performing the test.

SUMMARY OF THE INVENTION

These and other objects of the invention are achieved by providing a method and apparatus for ultrasonic detection of cracking in jet pump beams of a nuclear reactor. The apparatus holds ultrasonic transducers in position on a carriage lowered onto a jet pump beam to be examined. The carriage is remotely positioned onto the beam by maneuvering a pole connected to the carriage. Electric leads connect each of the ultrasonic transducers to a switching mechanism located external to the reactor vessel. The apparatus includes the switching mechanism and also a signal generator, receiver, and visual display. The method of using the apparatus involves directing a generated electric signal through the switching mechanism to a transducer mounted near the jet pump beam. The transducer converts the electric signal into an ultrasonic signal, which travels to an examination zone potentially containing cracks. Such cracks reflect or obstruct the passage of ultrasound. In one mode of operation, the sending transducer receives reflections from cracks. In another mode, an obstruction preventing reception of the transmitted signal indicates cracking.

DESCRIPTION OF PREFERRED EMBODIMENTS

Figure 1:
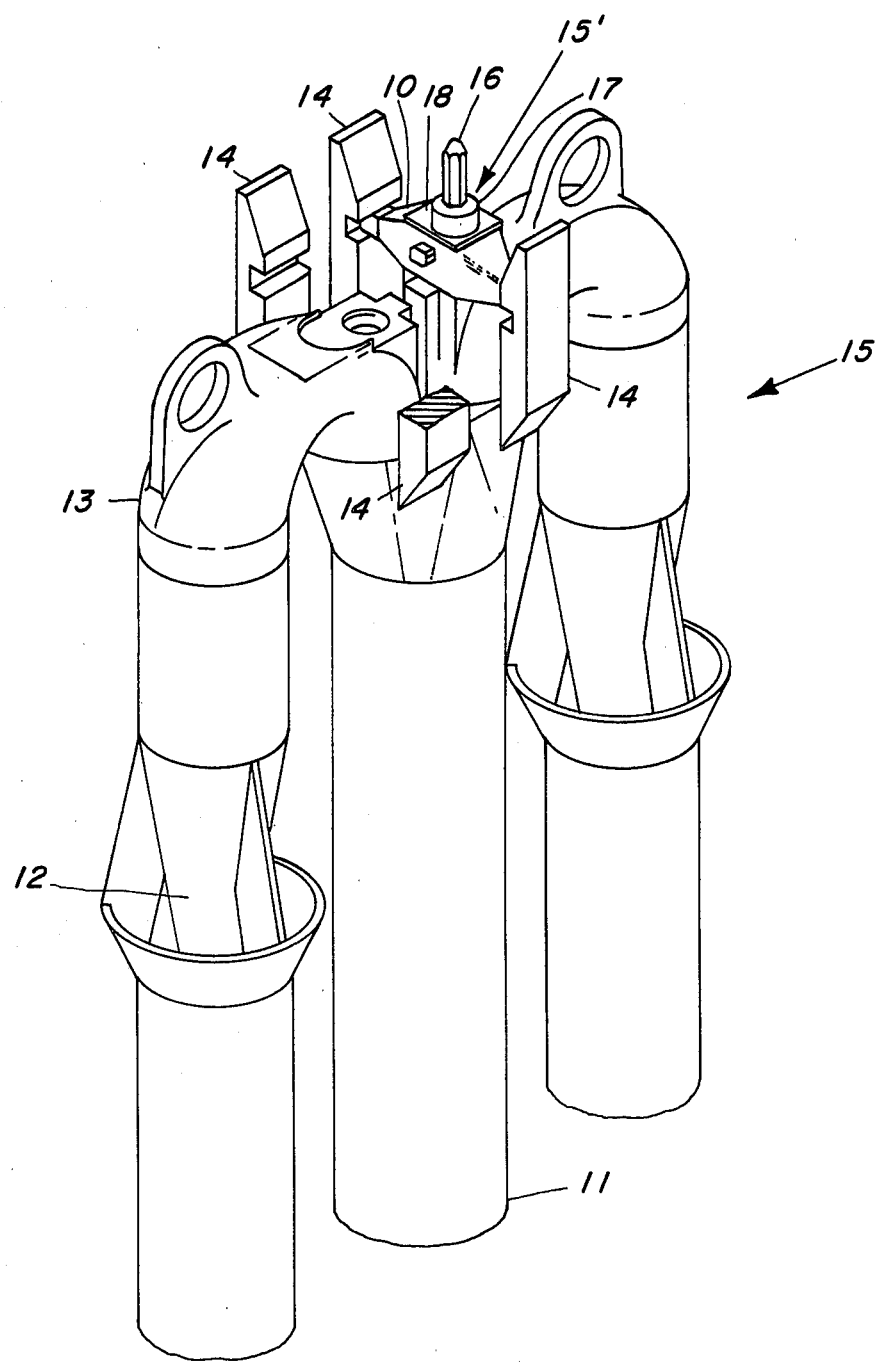
FIG. 1 is an isometric view of the upper portion of a jet pump assembly in a nuclear reactor, including the jet pump beam assembly.

The transducer apparatus described herein is constructed to be mounted on and to examine ultrasonically jet pump beams in nuclear reactors such as the beam 10 shown in FIG. 1. By way of background, the jet pump arrangement includes an inlet riser 11 which supplies pressurized driving water to a jet pump nozzle 12 through an elbow 13. The jet pump beam 10 is positioned between a pair of arms 14 extending from the inlet riser 11 and bearing against the elbow 13 to hold it in place. The jet pump beam 10, the arms 14, the elbow 13 and the inlet riser 11 are all part of the jet pump assembly 15 such as that shown in FIG. 1. Further details as to the construction and operation of such jet pumps are given in the previously mentioned U.S. Pat. Nos. 3,378,456 and 3,389,055 which are incorporated herein by reference.

Figure 2A:
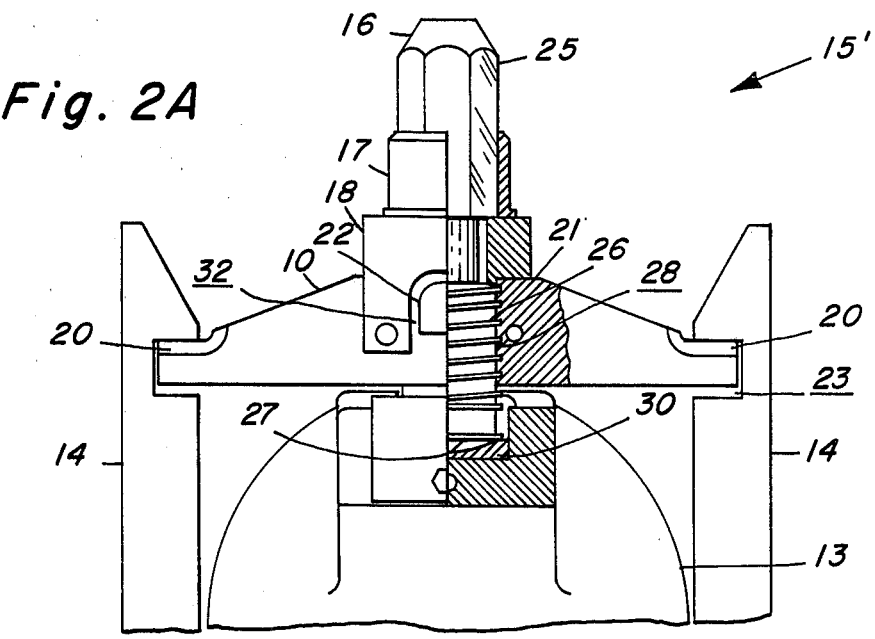
FIG. 2A is a side view of one version of a jet pump beam assembly, with a portion broken away, mounted at the top of the jet pump assembly, wherein the jet pump assembly includes a raised, U-shaped weld plate.

As FIG. 2A shows, a jet pump beam assembly 15' includes the beam 10, a beam bolt 16, a sleeve lock 17, and a weld plate 18. The beam 10 includes two ends 20, a raised central portion 21, and trunions 22. The ends 20 are supported in notches 23 of the arms 14 of the inlet riser 11. The bolt 16 includes a multisided head 25, threaded sides 26, and a butt end 27, which bears against a shoulder 30 of the elbow 13 (FIG. 1) of the jet pump assembly 15.

Figure 2B:
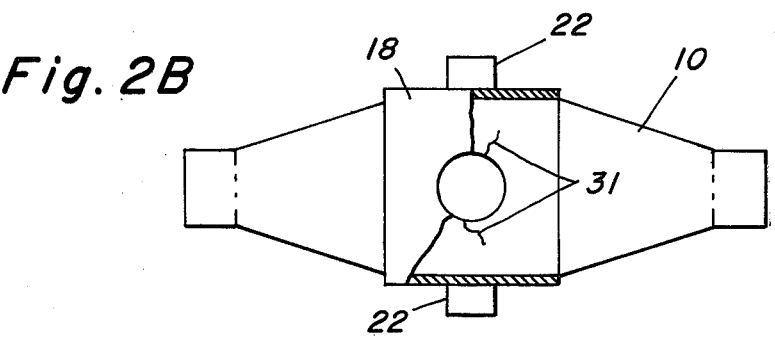
FIG. 2B is a plan view of the jet pump beam with a typical crack pattern illustrated on its top surface.

The beam bolt 16 passes through both the sleeve lock 17 and the weld plate 18, but whereas the weld plate 18 does not inhibit the bolt 16 from turning, the sleeve lock 17 slides snugly over the multisided head 25 of the beam bolt 16, and (after the bolt 16 is tightened) is tack welded onto the weld plate 18 to prevent bolt 16 from loosening. Because the bolt 16 is threaded through an aperture 28 of the beam 10 and applies an upward force on the beam 10, any cracks in the beam 10 are typically localized at the raised central portion of the beam 10, where the bolt 16 passes through, and extends toward the trunions 22 in the sides of the beam 10. A typical pattern of such cracks 31 is illustrated in FIG. 2B in a plan view of the jet pump beam 10 (with the weld plate 18 cut away).

The weld plate 18 shown in FIG. 2A is U-shaped, is suitably fixed onto the sides of the beam 10 and includes clearance bays 32 in the ends thereof for fitting around the trunions 22. The central portion of the weld plate 18 is disposed considerably above the beam 10 and allows access for the ultrasonic examination of the raised central portion 21 of the beam 10.

Figure 3:
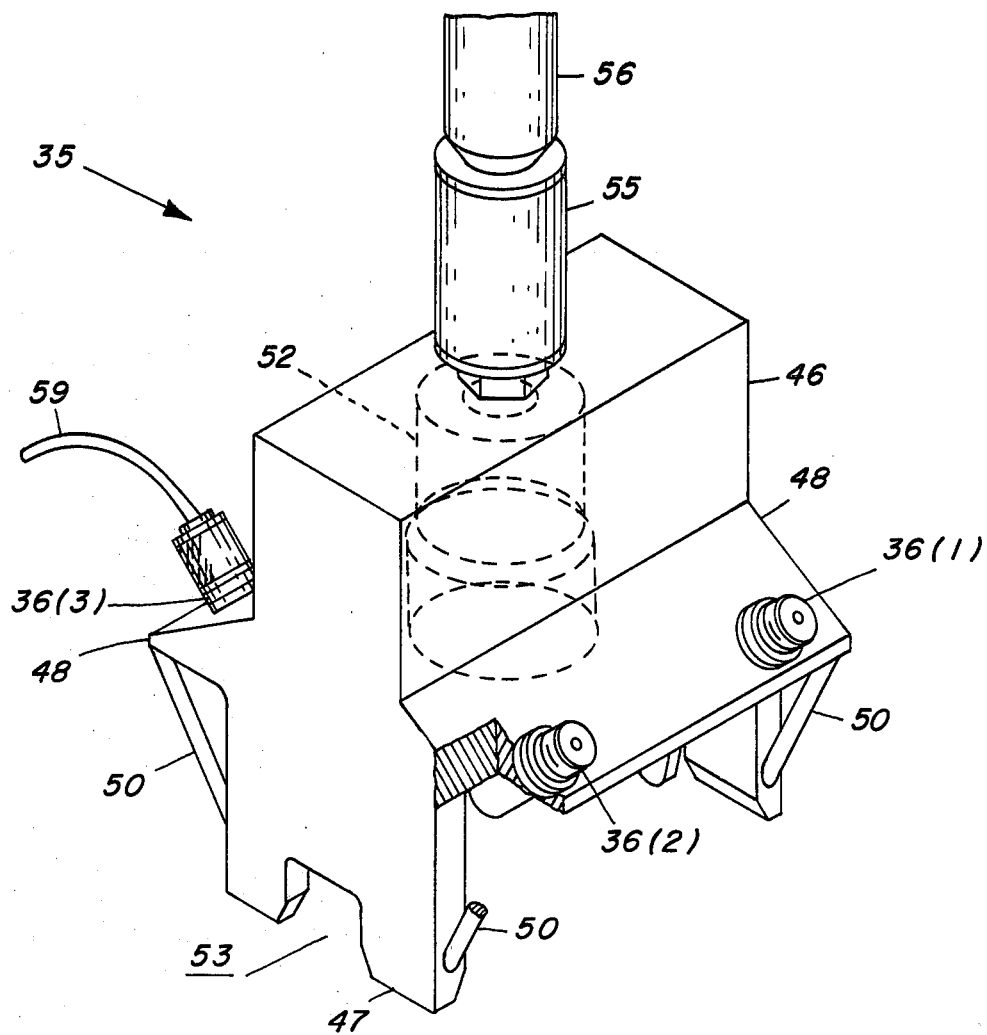
FIG. 3 shows the transducer carriage of the first embodiment, isometric view, suitable for mounting on a portion of the superstructure of a jet pump beam assembly such as that shown in FIG. 2A, by means of a positioning pole as partially shown.
Figure 4:
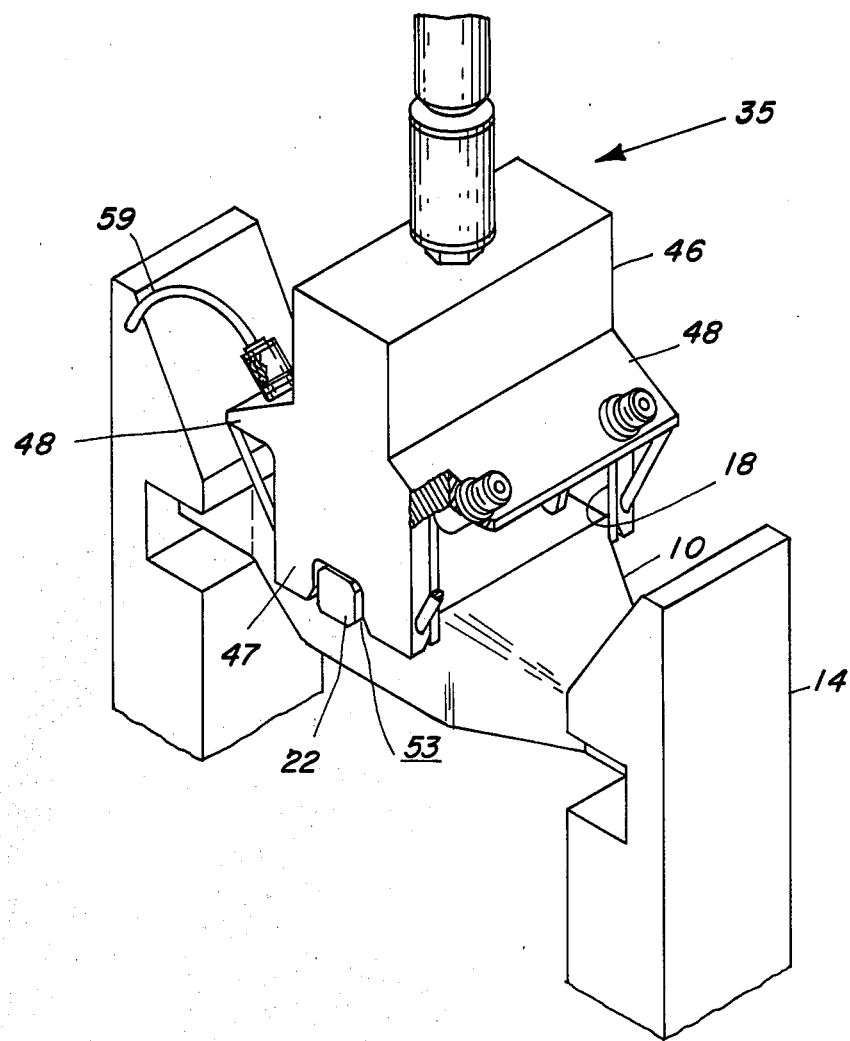
FIG. 4 shows an isometric view of the transducer carriage of FIG. 3 directly mounted on a jet pump beam.
Figure 5:
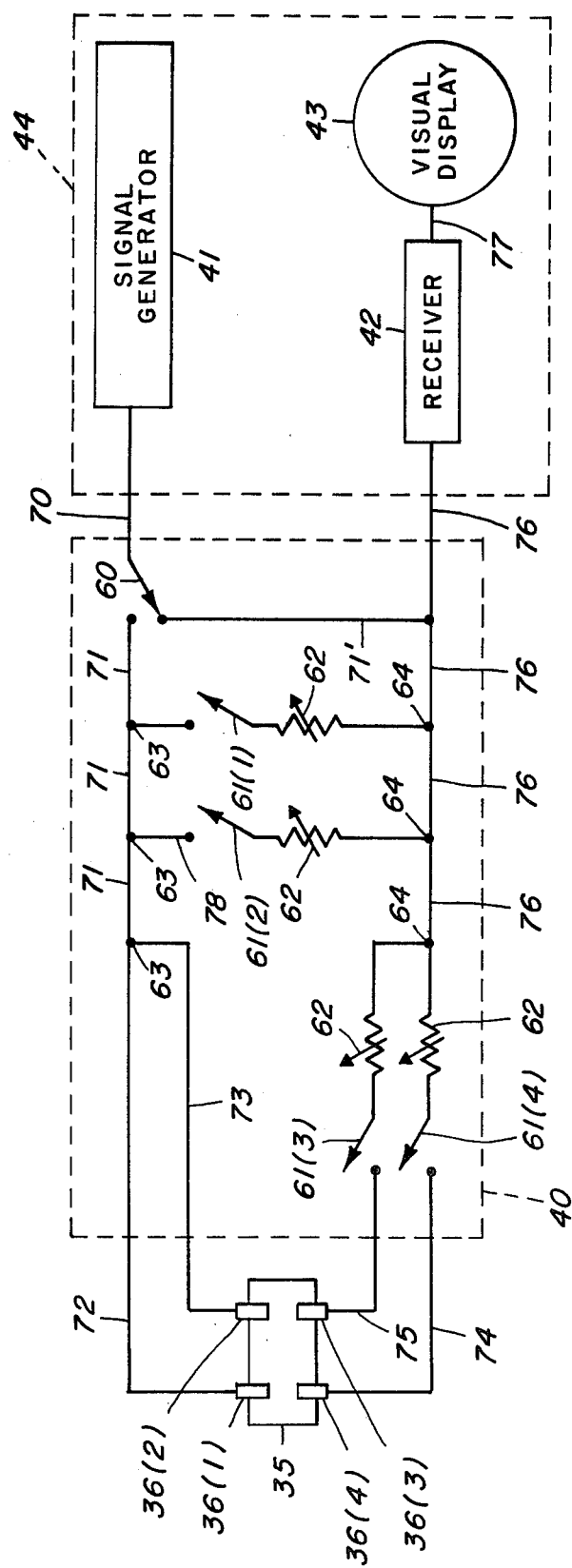
FIG. 5 is a schematic illustration of the ultrasonic apparatus, including switching circuitry mounted in a switch box for determining the mode of operation of the apparatus.

FIG. 3 depicts a part of the apparatus for ultrasonically examining the jet pump beam 10, namely a transducer carriage 35 for positioning a plurality of ultrasonic transducers 36 near the jet pump beam 10 just described. FIG. 5 schematically shows the entire transducer apparatus including a switching mechanism or box 40, a signal generator or ultrasonic transmitter 41, receiver 42, and visual display 43—the last three of which are available commercially in a single console 44. The transducer carriage 35 fits over part of the superstructure of the jet pump beam assembly 15', as shown in FIG. 4, and suitably orients the ultrasonic transducers 36 toward the raised central portion 21 of the jet pump beam 10.

The carriage 35 (FIGS. 3 and 4) comprises a central body 46 including extensions such as legs 47, wings 48, and struts 50, as well as a cavity 52 (shown in phantom), which is suitably fashioned in the underside of the central body 46 for receiving portions of the jet pump beam assembly 15', such as for example the upper parts of the beam bolt 16, sleeve lock 17, and weld plate 18. The legs 47 include recessed portions or bays 53 for cooperatively receiving the trunions 22 of the beam 10. Four transducers 36(1)–36(4), two on each side, are removably mounted in the wings 48 of the carriage 35 through cylindrical apertures of suitable diameter. Wing bolts (not shown) may conveniently removably secure the transducers 36 in the wings 48. The struts 50 between the ends of the wings 48 and the legs 47 protect the transducers 36 from damage in collisions that might occur when the carriage is lowered into the reactor vessel. The transducers 36(1)–36(4) in this embodiment are oriented downward 60° from the horizontal toward the center of the jet pump beam 10. Other suitable orientations may be utilized, depending on the position of the transducers 36 relative to the center of the beam 10.

The central body 46 of the transducer carriage 35 is preferably formed of aluminum, as are the wings 48 which extend outwardly from the body 46 for holding the transducers 36. Any convenient number of transducers 36 may be employed, but at least one is required and at least two are preferable.

Suitably mounted at the top of the central body 46 is a coupling device 55 which permits the attachment of the carriage 35 to a pole 56 or other device for lowering the carriage 35 into the reactor vessel and remotely manuvering the carriage 35 into position on a selected jet pump beam assembly 15'. The coupling device 55 may be fixed, permitting no relative motion between the pole 56 and the carriage 35, but it is preferable for the device 55 to be in the nature of a swivel or universal joint which permits limited pivotal motion of the carriage 35. This permits the carriage 35 to be properly seated on a jet pump beam 10, even though the mounting pole 56 is not in exact alignment with the beam 10.

An electrical lead 59 extends from each transducer 35(1)–36(4) toward the switching mechanism or box 40 shown in FIG. 5, which is located external to the reactor vessel. Conveniently, the switching mechanism 40 may be located in the immediate proximity of the console 44 which houses the signal generator 41, receiver 42, and the visual display 43. One example of such console 44 is the Krautkramer USIP11. Transducers suitable for use in this embodiment of the invention are manufactured by Ultran Laboratories under Part No. WS.5-2.25 MHZ.

FIG. 5 shows the circuitry within the switching box 40, including a mode switch 60, four transducer switches 61(1)–61(4), four current limiting variable resistors 62, and terminals 63, leading a signal toward transducers 36(1) and 36(2).

Accordingly, either transducer 36(3) and 36(4) may receive the transmitted signal and transfer it by leads 74 or 75, and 76 to receiver 42 and the visual display 43. In this mode of operation, switches 61 (1) and 61(2) are open, and one of the switches 61(3) and 61(4) is closed. The corresponding variable resistor 62 may be adjusted to enhance or reduce the signal level in the visual display 43.

In the "pulse-echo" mode, switch 60 directs a signal from the ultrasonic transmitter 41 through lead 71' to terminal 64. A selected one of switches 61(1)–(4) is closed, determining which of the transducers sends and receives the signal generated by the transmitter 41. The transmitter 41 and receiver 42 are staggered in time of operation, preventing the transmitter signal from passing along the path of leads 71' and 76. In other words, the receiver 42 is "off" or disabled during the time fraction in which the transmitter sends its signal.

Terminal 63 connecting leads 72 and 73 considerably simplifies the switching arrangement, avoiding possible attempts to switch non-cooperating transducers together in the "thru" mode. Since transducers 36(1) and 36(2) both send a signal when either of them sends a signal, switching to either transducer 36(3) or 36(4) provides meaningful information on the visual display 43.

By suitably closing switch 60 to one of its two contacts and also closing a selected one or two of switches 61(1) through 61(4), the desired mode of operation (thru or pulse-echo) may be established. The "thru" mode is set by closing switch 60 to the upper contact shown in FIG. 5 and by additionally closing either switch 61(3) or 61(4) of the set of switches 61(1)–61(4) and keeping the remainder of the switches in the set open. The "pulse-echo" mode, on the other hand, is set by closing switch 60 to the lower contact shown in FIG. 5 and by additionally closing exclusively a selected one of switches 61(1) through 61(4).

For ultrasonic examination, the carriage 35 is lowered into the reactor vessel, with the electric leads 59 streaming behind, and is straddlingly mounted on a selected beam 10. The legs 47 of the carriage 35 straddle the beam 10, as shown in FIG. 4, and the bays 53 of the legs 47 are seated on the trunions 22 of the beam 10. Furthermore, portions of the bolt head 25 and the sleeve lock 17 of the jet pump beam assembly 15' are disposed within the cavity 52 of the central body 46 of the carriage 35. So positioned, the transducers 36(1)–36(4) held in the wings 48 of the carriage 35 are properly oriented from above and toward the jet pump beam 10, and under the central portion of the U-shaped weld plate 18, to effect a proper ultrasonic examination of critical beam regions.

By energizing the ultrasonic console 44 and manually selecting one or more transducers 36 for sending and receiving ultrasonic signals, actual test operation can commence.

In particular, the switching mechanism 40 permits a selected one or two of the transducers to be operative either individually or in pairs. As noted above, the transducers 36(1)–36(4) are oriented from above in this embodiment in a form of examination commonly known as "critical angle surface examination." The angle of incidence of the ultrasonic signal to the horizontal upper surface of the beam is 60°. In the "pitch-catch" mode, as it is often referred to, two of the transducers 36(1)–36(4) cooperate, one sending an ultrasonic signal and the other receiving it after passage along the top surface of the beam 10. Cracks in the surface of the beam inhibit a signal sent by the "pitch" transducer from substantially reaching the "catch" transducer 36. Whatever signal is received by the "catch" transducer is shown on the visual display 43 of the console 44, permitting an indication of the position and extent of a crack.

In the "pulse-echo" mode of operation, the selected one of the transducers 36(1)–36(4) both sends and receives ultrasonic signals. A return signal is received only when the transmitted signal is substantially reflected from a crack.

Figure 6:
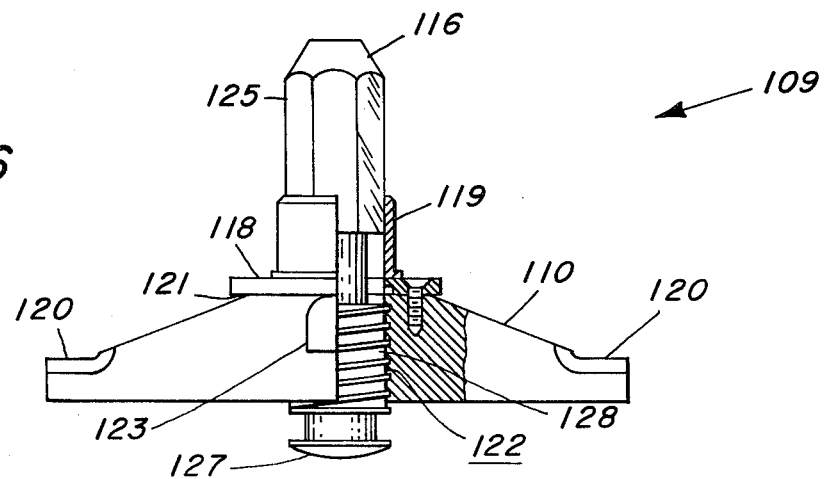
FIG. 6 is a side view of a second embodiment of a jet pump beam assembly, with a portion thereof broken away, disclosing a flat weld plate.

A second version of embodiment of a jet pump beam assembly 109 is shown in FIG. 6. In this version the assembly 109 includes a beam 110, a beam bolt 116, a weld plate 118, and a bolt lock 119 similar to the assembly 15' discussed above. The beam 110 includes two ends 120 and a raised central portion 121. Additionally, the beam includes a vertically directed, threaded cylindrical aperture 122 in the central raised section 121 and between the two ends 120. Furthermore, a pair of oppositely disposed trunions 123 extend from the sides of the beam 110. The bolt 116 includes a multisided head 125, a butt end 127, and a threaded midsection 128 of diameter, thread size, and pitch to mesh cooperatively with the threaded cylindrical aperture 122 of the beam 110 mentioned above.

However, the weld plate 118 is flat, rather than U-shaped as in the first embodiment and it is mounted flush with the central raised portion 121 of the beam 110. A circular aperture in the weld plate 118 permits the beam bolt 116 to pass through without obstruction. The bolt lock 119 is in the form of a sleeve fitting over the multisided head 125 of the beam bolt 116. Additionally, the bolt lock 119 is tack welded onto the weld plate 118, and thereby locks the bolt 116 onto the beam 110. The beam assembly 109 is mounted in notches 23 of the arms 14 of the inlet riser 11 (shown in FIG. 1), and the butt 27 of the beam bolt 116 bears downward on a shoulder 30 of pipe elbow 13, thereby holding it in place in the jet pump assembly 15.

Figure 7:
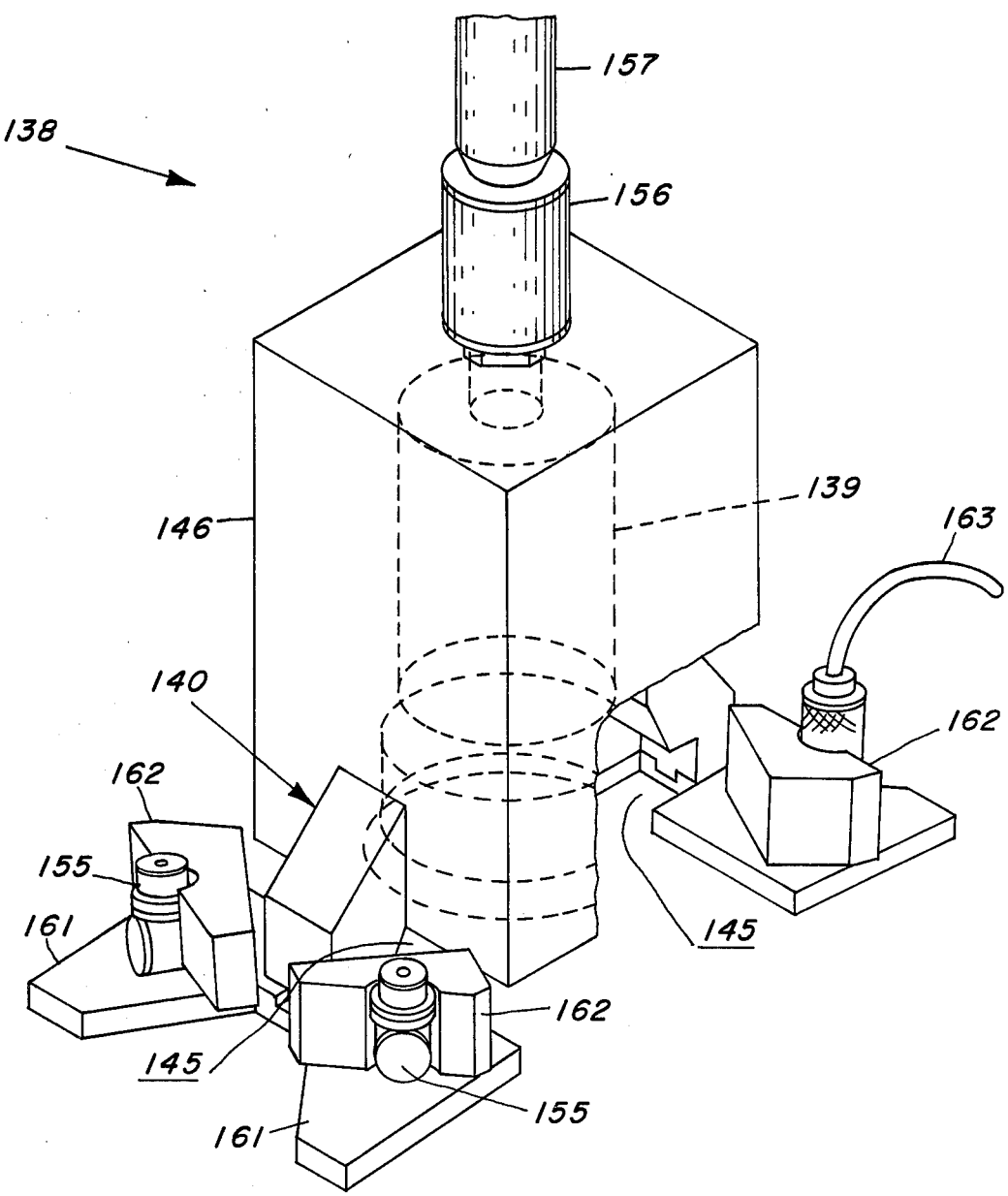
FIG. 7 shows an ultrasonic transducer carriage in isometric view suitable for mounting a jet pump beam of the embodiment of FIG. 6.
Figure 8:
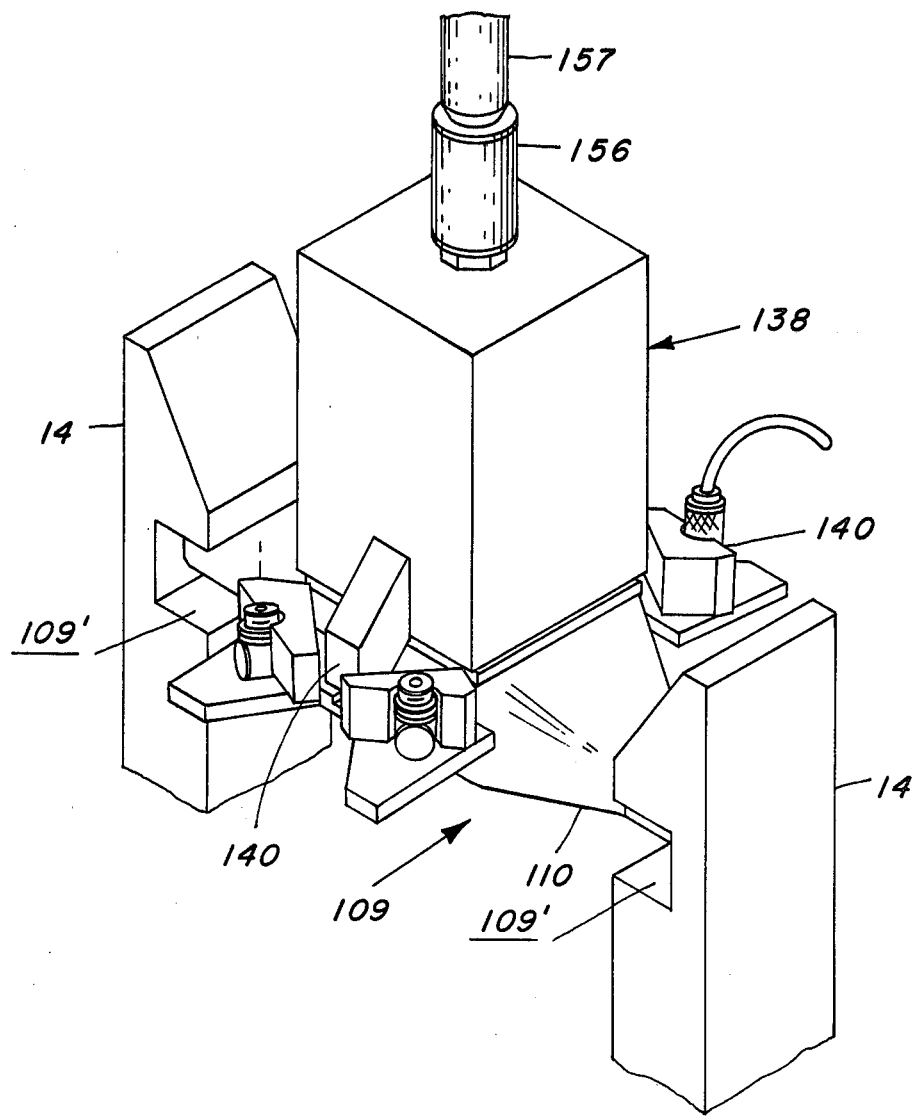
FIG. 8 shows an isometric view of the transducer carriage of FIG. 7 mounted on the jet pump beam of FIG. 6.

A second version of the transducer carriage 138, particularly adapted to examine the version of the beam assembly 109 just discussed, is described immediately hereafter in conjunction with FIGS. 7 and 8. A cavity 139 in the underside of the carriage 138 fits over part of the superstructure of the jet pump beam assembly 109 just including the flat weld plate 118 (FIG. 6). Furthermore, extensions such as wings 140 of the carriage 138 extend below the raised central portion 121 of the beam 110 in order to examine the beam 110 for cracks from below. This is necessary since the flat weld plate 118 obstructs examination from above. The second version of the transducer carriage 138 includes a central body 146 from which the two wings 140 extend. Each of the wings 140 holds a pair of transducers 155 and each such wing has a recessed portion 145 for placement on the trunions 123. However, any suitable number of transducers may be mounted in the carriage 138.

The carriage 138 includes a coupling device 156 mounted preferably near the center of its upperside. The coupling device 156 connects to a pole 157 or like device, for lowering the carriage 138 into the reactor vessel. The coupling device 156 may be of any suitable kind including a swivel or universal joint type device as mentioned hereinbefore in connection with coupling 55 of FIG. 3. Transducers 155 of any suitable kind are provided for transmitting and receiving ultrasonic signals. For this embodiment, an Ultran Laboratories PS.5-2.25 MHZ transducer is suggested.

The wings 140 extend below the raised central portion 121 of the beam 110, as shown in FIG. 8, and each wing 140 includes a horizontal wing plate 161 having two blocks 162 suitably mounted on each wing plate. Each block 162 is formed with an internal approximately horizontal aperture for receiving and mounting a transducer 155 by insertion. Each of the transducers 155 is directed toward the region of the beam 110 most susceptible to cracking. Accordingly, the transducers 155 are specifically aimed toward the raised central portion 121 of the beam 110 at an angle of about 65° from a vertical plane defined by the axis of the beam 110. Additionally, the transducers 155 are horizontally mounted about 0.1 inches below the raised central portion 121 of the beam 110. In the alternative, the transducers 155 can be tilted slightly upward from the horizontal, as for example, by 10° in order to focus from below at the upper surface of the beam 110.

The transducers 155 of the carriage 138 may be connected for operation in conjunction with the ultrasonic apparatus of FIG. 5 by substituting the electrical connections thereto (i.e., leads 163) for the connections to the transducers 36 therein shown.

In operation, a technician lowers the transducer carriage 138 into a reactor vessel by pole 157. He maneuvers the carriage 138 into position whereby it straddlingly mounts the beam assembly 109 as shown in FIG. 8. In particular, the cavity 139 in the central body 146 sits over the head 125 of the beam bolt 116 and notches 145 in the wings 140 engage the trunions 122 in the beam 110. In this manner, the four transducers 155 in the instant embodiment are suitably positioned relative the jet pump beam 110 for ultrasonic examination.

To begin examination, the signal generator 41 (FIG. 5) is energized, and the switching mechanism 40 is suitably manually set to allow the signal generator 41 to provide an electric signal to a chosen transducer 155. This signal is converted into an ultrasonic signal impinging on the side of the beam 110, which refracts from a longitudinal wave into a shear wave according to Snell's law and continues on a path without reflection until a crack 31 is met. This form of ultrasonic examination in which the ultrasonic shear wave signal travels within the body tested is known as "shear wave" examination.

Depending on the arrangement selected by the switching mechanism 40, the receiver 42 can receive either an "echo" of the generated signal impinging on a crack, or the remnant of the transmitted signal. In the latter case, a second usually oppositely disposed transducer 155 must be used in cooperation with the first. As noted earlier, using two transducers 155—one to send, and one to receive—is known as the "pitch-catch" mode of operation.

Once a given jet pump beam has been tested, the technician may remove the carriage to another beam and repeat the entire operation described above. Typically, the operation is repeated approximately 20 times in each reactor, once for each jet pump beam.

After reference to the foregoing, modifications of this invention may occur to those skilled in the art. However, it is to be understood that this invention is not intended to be limited to the particular embodiment shown and described herein, but is intended to cover all modifications coming within the spirit and scope of the invention claimed.

What is claimed is:

1. An apparatus for detecting cracks in the jet pump beam of a jet pump arrangement of a nuclear reactor, wherein said arrangement includes a downwardly directed jet pump having a nozzle for receiving pressurized driving water, a riser pipe positioned adjacent said jet pump for supplying said driving water, a pipe elbow connecting the top of said riser pipe to the inlet of said nozzle, and a removable jet pump beam assembly, including a jet pump beam bearing on said elbow to hold said elbow in place, said apparatus comprising an ultrasonic signal production means, and communicating means for communicating said signals from said production means to and from a jet pump beam, said communicating means being straddlingly mountable over a jet pump beam, and said ultrasonic signals being directionally oriented toward the upper surface of said jet pump beam, whereby incipient cracks appearing on said surface are timely ultrasonically detectable.

2. The apparatus of claim 1, wherein said communicating means includes at least one ultrasonic transducer and a transducer carriage for holding and positioning said at least one ultrasonic transducer for communication with said jet pump beam.

3. The apparatus of claim 1, further comprising transfer means transferring ultrasonic signals from said communicating means to a visual display, whereby electric signals indicative of cracking in said jet pump beam are conveniently displayed through a viewer.

4. The apparatus of claim 2, wherein at least two oppositely disposed ultrasonic transducers are held by said transducer carriage and one of said transducers sends ultrasonic signals and the other receives a portion of said signals.

5. The apparatus of claim 2, wherein the number of ultrasonic transducers is four, each of them being a member of a pair of oppositely disposed ultrasonic transducers.

6. The apparatus of claim 5, wherein one of said members of a pair is effective for sending and the other of said members is effective for receiving ultrasonic signals.

7. The apparatus of claim 5, wherein each of said transducers is effective for sending and receiving ultrasonic signals, whereby information indicative of cracking in said jet pump beam is produced.

8. The apparatus of claim 1 comprising positioning means for remotely positioning said communicating means and to straddlingly mount such jet pump beam including connection means for mechanically connecting said communicating means to said positioning means.

9. The apparatus of claim 8, wherein said connection means permits relative motion between said positioning means and said communicating means, whereby the vertical axis of said communicating means is adjustable to define an acute angle between the longitudinal axis of said positioning means and the vertical axis of said communicating means.

10. The apparatus of claim 8, wherein said positioning means is an elongated extension pole.

11. The apparatus of claim 1, wherein said communicating means defines a cavity fitting over a jet pump beam assembly and includes oppositely disposed extensions effective for straddling the sides of said jet pump beam assembly.

12. The apparatus of claim 11, wherein said communicating means is constructed in part from a block of aluminum.

13. An apparatus for detecting cracks in the jet pump beam of a jet pump arrangement of a nuclear reactor, wherein said arrangement includes a downwardly directed jet pump having a nozzle for receiving pressurized driving water, a riser pipe positioned adjacent said jet pump for supplying said driving water, a pipe elbow connecting the top of said riser pipe to the inlet of said nozzle, and a removable jet pump beam assembly including a jet pump beam bearing on said elbow to hold said elbow in place, said apparatus comprising:
 a plurality of transducers and electric circuitry for communicating an ultrasonic signal between a signal generator and a jet pump beam, said transducers arranged in oppositely disposed pairs;
 a carriage for positioning said plurality of transducers toward and in the proximity of said jet pump beam, and defining a cavity on its underside and including lateral extensions for cooperatively engaging the superstructure of a jet pump beam assembly including the jet pump beam; and
 pole means including adjustable connecting means connected to the upper portion of said carriage and responsive to the orientation of the jet pump beam assembly and the longitudinal axis of said pole means, whereby said pole means is effective for the remote positioning of said carriage and transducers on said jet pump beam assembly.

14. The apparatus of claim 13, wherein said carriage includes wings for mounting said transducers.

15. The apparatus of claim 13, wherein said transducers are mounted in said lateral extensions of said carriage.

16. The apparatus of claim 13, wherein said electric circuitry includes switching means permitting the manual selection between individual and pairs of transducers for sending and receiving ultrasonic signals in communication with said jet pump beam.

17. The apparatus of claim 13, wherein said extensions rest on trunions of said jet pump beam assembly and said extensions each include a recessed portion for cooperatively receiving one of said trunions.

18. The apparatus of claim 13, wherein the transducers are disposed to communicate an ultrasonic signal toward the jet pump beam and from above the upper surface of the jet pump beam.

19. The apparatus of claim 13, wherein the communicated ultrasonic signal penetrates the sides of the jet pump beam and examines the upper surface thereof.

20. The apparatus of claim 13, wherein the transducers are downwardly oriented about 60° from the horizontal.

21. The apparatus of claim 13, wherein the transducers are upwardly oriented 10° from the horizontal and inwardly 65° from a vertical plane through the central axis of the jet pump beam.

22. An apparatus for detecting cracks in the jet pump beams of a jet pump arrangement of a nuclear reactor, wherein said arrangement includes a downwardly directed jet pump having a nozzle for receiving pressurized driving water, a riser pipe positioned adjacent said jet pump for supplying said driving water, a pipe elbow connecting the top of said riser pipe to the inlet of said nozzle, and a removable jet pump beam assembly, including a jet pump beam bearing on said elbow to hold said elbow in place, said apparatus comprising:
 a plurality of ultrasonic transducers directed at the upper surface of a jet pump beam,
 a transducer carriage for holding and directing said plurality of transducers,
 a positioning pole for remotely mounting said transducer carriage on said jet pump beam,
 an adjustable joint means connecting said positioning pole to the upper portion of said transducer carriage;
 whereby said transducer carriage is mounted on a jet pump beam and in ultrasonic communication therewith.

23. The apparatus of claim 22, wherein said adjustable joint means includes a swivel joint and a restraining means for providing an aligning bias between the vertical axis of the transducer carriage and the longitudinal axis of the positioning pole.

24. The method of examining the upper surface of a jet pump beam for incipient cracks, including the steps of remotely positioning a plurality of ultrasonic transducers near the jet pump beam while installed in a nuclear reactor, sending an ultrasonic signal toward the upper surface of said jet pump beam, receiving a portion of said signal, and visually displaying the received portion of the signal.

25. The method of claim 24, wherein the same transducer is effective for sending the ultrasonic signal and receiving a portion thereof.

26. The method of claim 24 including the step of inserting the plurality of transducers in a carriage and lowering said carriage into the reactor vessel for straddlingly mounting said jet pump beam.

* * * * *